United States Patent [19]

Wyrwich et al.

[11] Patent Number: 4,599,800
[45] Date of Patent: Jul. 15, 1986

[54] CALIPER FOR MEASURING DEFORMABLE OBJECTS

[75] Inventors: Helmut Wyrwich, Jülich, Fed. Rep. of Germany; Georgi Graschew, Sofia, Bulgaria; Johann Chatzipetros, Frechen; Ludwig E. Feinendegen, Jülich, both of Fed. Rep. of Germany

[73] Assignee: KFA—Kernforschungsanlage Julich GmbH, Jülich, Fed. Rep. of Germany

[21] Appl. No.: 612,568

[22] Filed: May 21, 1984

[30] Foreign Application Priority Data

May 24, 1983 [DE] Fed. Rep. of Germany ....... 3318823
Mar. 22, 1984 [DE] Fed. Rep. of Germany ....... 3410509

[51] Int. Cl.⁴ ............................ G01B 3/24; G01B 5/06
[52] U.S. Cl. ................................... 33/143 C; 33/147 F
[58] Field of Search ............. 33/143 C, 147 R, 147 F, 33/147 H, 172 E

[56] References Cited

U.S. PATENT DOCUMENTS

| | | | |
|---|---|---|---|
| 2,810,200 | 10/1957 | Delaney | 33/147 F |
| 3,483,626 | 12/1969 | Huttel | 33/172 E |
| 3,987,552 | 10/1976 | Raiteri | 33/172 E |
| 4,389,783 | 6/1983 | Sakata et al. | 33/143 L |
| 4,420,887 | 12/1983 | Sakata et al. | 33/147 F |
| 4,492,034 | 1/1985 | Nishina et al. | 33/172 E |

FOREIGN PATENT DOCUMENTS

| | | | |
|---|---|---|---|
| 2832986 | 2/1980 | Fed. Rep. of Germany . | |
| 3045355 | 9/1981 | Fed. Rep. of Germany . | |
| 173708 | 10/1982 | Japan | 33/172 E |
| 853357 | 8/1981 | U.S.S.R. | 33/147 F |

OTHER PUBLICATIONS

"Feinmesszeuge" published by Mauser-Messzeugg M.B.H., 8-1972.

Primary Examiner—Richard R. Stearns
Attorney, Agent, or Firm—Karl F. Ross; Herbert Dubno

[57] ABSTRACT

A caliper for soft objects such as tumor tissue has a pair of contact plates on respective members of which at least one is movable so that the object can be embraced between the contact plates. The instrument has a visual display of the contact pressure, an electrical display of the contact pressure or a locking mechanism establishing the contact pressure for reproducible measurement.

11 Claims, 10 Drawing Figures

CALIPER FOR MEASURING DEFORMABLE OBJECTS

FIELD OF THE INVENTION

Our present invention relates to a device for measuring the size of easily deformable objects, and, more particularly, to a caliper-type instrument having a pair of relatively movable sensing arms between which the object is engaged and an indicator for signaling the distance between the sensing ends of these arms. The invention is especially intended to measure the size of such highly deformable objects such as a body of tumor tissue.

BACKGROUND OF THE INVENTION

The measurement of size of rigid objects with screw-type micrometers, pivotal caliper devices and sliding calipers is relatively simple since the degree of contact with the object can be readily determined by the user with some experience and utilizing the touch sensation only.

For yieldable objects such as foam material, rubber or elastomeric materials, the results of such measurements are highly dependent upon the force with which the caliper members bear upon the object. In these cases and in the measurement of tissue thicknesses, especially tumor tissue size, the variations in measurement can be comparatively large because of the sensitivity of the object to compression. The calipers utilized for this purpose in the past have included sensing arms which were urged against the tissue by the hand of the surgeon or a helper. When various individuals attempt to take the measurement, a variety of results generally will be obtained.

OBJECTS OF THE INVENTION

It is, therefore, the principal object of the present invention to provide an improved device for measuring the size of soft compressible objects such as bodies of tumor tissue whereby the disadvantages of such earlier systems can be overcome.

Another object of this invention is to provide a tumor measuring caliper which can provide highly accurate results and which has largely excluded subjective effects upon the measurements.

Still another object of the invention is to provide a measuring caliper of the type described which can be utilized with comparatively soft materials and whereby a given measurement pressure can be assured so that reproducible measurement operations can be effected.

SUMMARY OF THE INVENTION

These objects and others, which will become apparent hereinafter, are attained in accordance with the present invention in a device for measuring the size of easily deformable objects, especially tumors or other animal tissue, having a pair of relatively displaceable arms with object-contacting ends whose spacing displayed or indicated upon a scale to which these arms are coupled. For the purpose of this coupling, one of these arms may be fixed to the scale bed while the other of the arms is movable relative to the fixed arm and operates the movable member of the scale.

According to the present invention, the contact ends of the arms are each provided with a respective contact plate and the contact plate is displaceable relative to the respective end of the arm against the force of a spring which acts upon the plate to resist this displacement. The arms are provided with means for indicating or establishing a fixed pressure of each plate, this means including, for example, a detent, lock or like device for fixing the contact pressure and/or a signaling device capable of generating an output when the desired measurement pressure is achieved and/or a display directly reading in terms of contact pressure.

Through the use of this display, signaling device and/or detent or locking system, the measurement can be read from the scale as soon as the desired measurement force or pressure is generated by the plate against the tissue and hence between the end of the arm and the plate carried thereby.

According to a feature of the invention, the contact plate is carried by a rod or shank which is slidable in the end of the respective arm and against which the spring is seated, this rod carrying an indicator whose position with respect to a scale can display a measurement or parameter proportional to the contact pressure so that the attainment of the desired contact force can be ascertained.

Specifically, an elongated slot can be formed in the respective end of the arm and can be traversed by a pin transverse to the rod whose end is notched or otherwise provided with an indicating symbol cooperating with a scale formed on the arm along one side or flank of the slot.

In addition or alternatively, the rod can be provided with an electrical contact or circuit which triggers a signal through an appropriate circuit as an indicator to the user that the desired pressing force has been reached.

According to another feature of the invention, each sensing arm can be provided with a slidable rod or bar thereon upon which the contact plate is mounted, a biasing coil spring, and means for coupling the plate to the rod when the desired pressing force (and degree of compression of the spring) is achieved. The rod or slider can be provided with a restoring spring urging the slider into its position of maximum plate separation.

The spring which yields as the pressing force increases can be provided, according to the invention, with an adjustable seat, the position of which can vary the desired measurement force. In addition or alternatively, a form-fitting lock or detent can be provided to lock the sensing arm and the contact plate rod or slider.

According to another feature of the invention, the form-locking detent comprises a pawl mechanism which engages a lever connected with the end of the force-generating spring and which engages at the selected degree of coupling of this spring in a tooth or notch formed by a rack or a detent pinion which can be connected with the face.

Since the pressure sensitive detent engagement of the sensing arm should allow a fine distinction between points of engagement over the entire measurement range, preferably the detent includes a detent pinion which restricts the movement of the sensing arm and especially can be fixed to the indicator rod of a dial indicator fixedly connected to the sensing arm. The detent mechanism embraces a rotatable pivot lever journaled in the housing and, with the aid of a compression-spring-actuated lever or ratchet, causes the pawl to engage in the detent wheel or pinion.

To this end, the lever can have a longitudinal groove in which a pin of the lever sits, the tilting plate of the lever and the ratchet being then perpendicular to one another.

The desired measuring force is especially selectable by an appropriately adjustable pre-compression of the spring against its seat and advantageously the spring and detent mechanism are located within the scale housing which is preferably a dial indicator housing so that dust and contaminants are prevented from interacting with them.

BRIEF DESCRIPTION OF THE DRAWING

The above and other objects, features, and advantages of the present invention will become more readily apparent from the following description, reference being made to the accompanying drawing in which.

SPECIFIC DESCRIPTION

Figure 1:
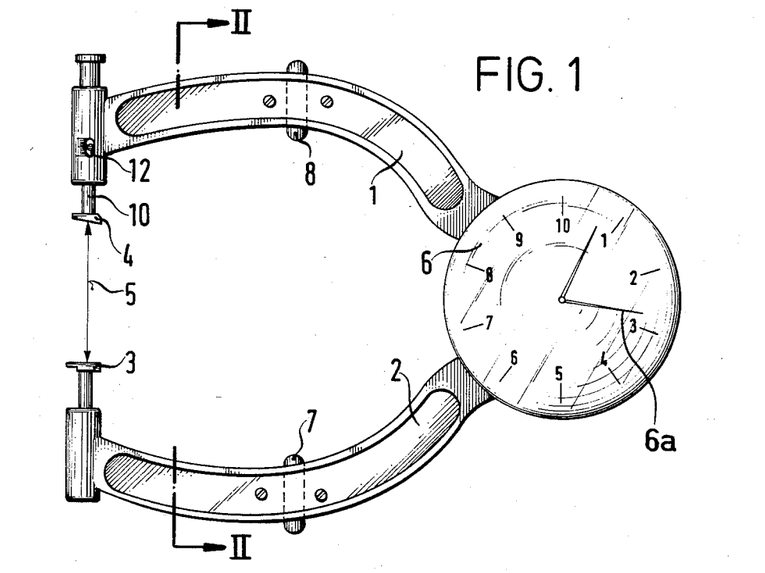
FIG. 1 is an elevational view of a caliper-like thickness measuring instrument according to the invention.
Figure 2:
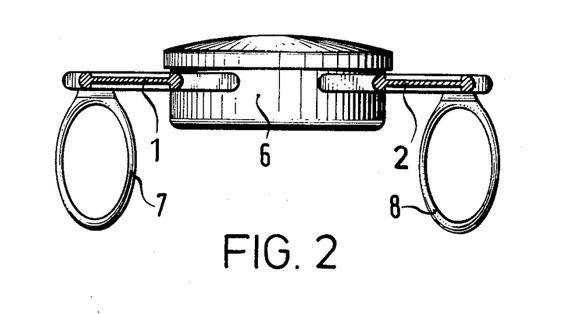
FIG. 2 is a cross-sectional view taken along the lines II—II of FIG. 1.

As can be seen from FIGS. 1 and 2, the caliper of the invention can comprise a pair of sensing arms which are relatively movable and one of which can be fixed to the housing 6 of an indicator unit, while the other is connected to the gearing or other internal mechanism of this indicator which can have indicating hands 6a for displaying the spacing between the free ends of these arms 1 and 2. Since the construction of the dial indicator 6, 6a is well known in the art, no separate description thereof is required herein. The dial indicator 6, 6a, of course, can be provided with any desired scale in any desired measurement system for displaying the measurement.

The free ends of the arms 1 and 2 are provided with contact plates between which the tissue is engaged by finger rings 7 and 8 so as to enable the surgeon or a surgical attendant to draw the arms 1 and 2 together after the thumb and index finger have been inserted into the rings.

It will be apparent that the measurement displayed on the scale is a function of the pressure with which the tissue is engaged by the contact plates 3 and 4. To ensure that the measurement will be reproducible or in accord with a standard, one or both of the contact plates can be provided at the end of a rod 10 (see FIG. 3) guided in the sleeve 11 via the bushing 11a at the free end of the arm (e.g. arm 1). The rod 10 has a shoulder 10a against which a spring 9 rests, the spring 9 being adjustably seated (by the screw 13) in the sleeve 11. The screw 13 also forms a guide for the shank of this rod. Thus, the force of the spring 9 can be adjusted.

Figures 3, 4:
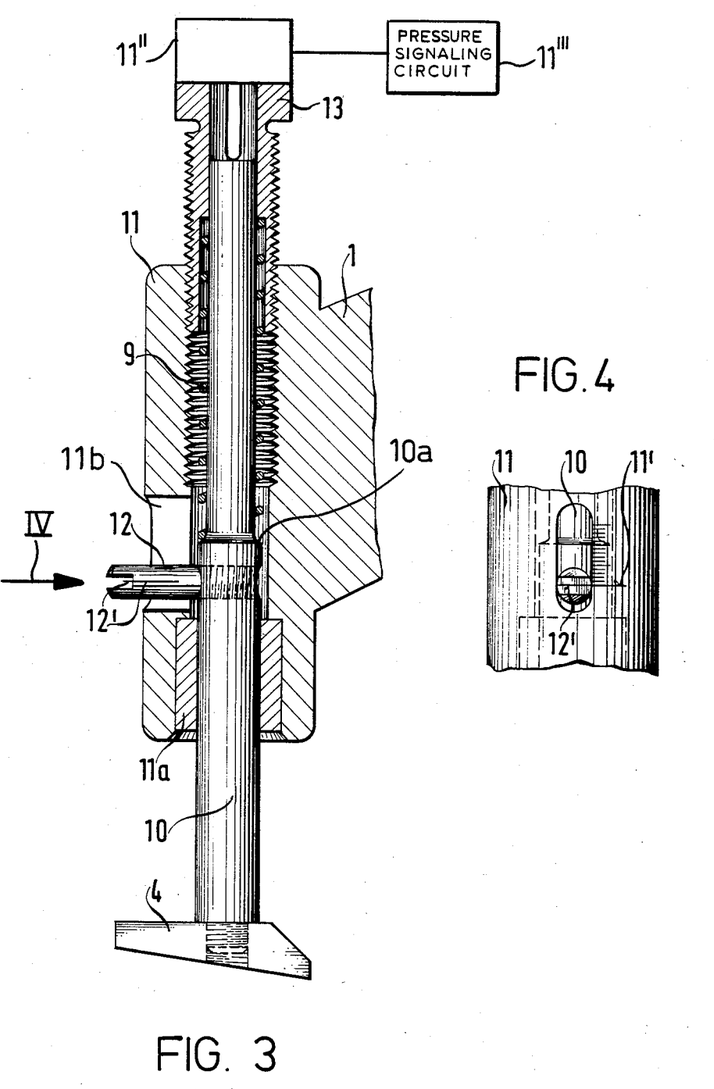
FIG. 3 is a detailed view representing an axial section through the free end of one of the measuring arms showing the contact plate and its slidable support rod.
FIG. 4 is a view generally in the direction of the arrow IV illustrating a force-level indicator for the contact plate.

The rod 10 is provided with a pin 12 which projects through slot 11b and along a flank where a scale 11' is provided, e.g. by engraving or embossing. This scale can be provided as a Vernier scale and can cooperate with indicia of the pin 12. In this case, the indicia is represented as a notch 12' (see FIG. 4).

Utilizing the indicator formed at 11', 12', the operator can determine the exact contact pressure for a given reading of the scale 6, 6a upon which the measurement is taken.

Instead of the simple visual signal provided by the scale 11', 12', or in addition thereto, a switch or linear potentiometer 1" can be mounted on the device to respond to the position of the rod or spindle 10 and can be connected to an electronic circuit 11'''. The means 11" and 11''' forms an electronic contact or circuit system which can provide an optical or acoustical signal when the appropriate contact pressure is reached so that the reading may be taken and can in addition provide an automatic registration of the measured value at appropriate contact pressure.

The circuit can work into a memory or electronic storage which can form a mean value of a measurement, the latter being modified by an error value which can be calculated from any excess contact pressure or contact pressure deficiencies.

The calipers described hereinafter can likewise be provided with such circuitry.

The requisite contact pressure at the instant of reading can be easily varied via the thimble 13 and hence the change in spring pressure.

Figure 5:
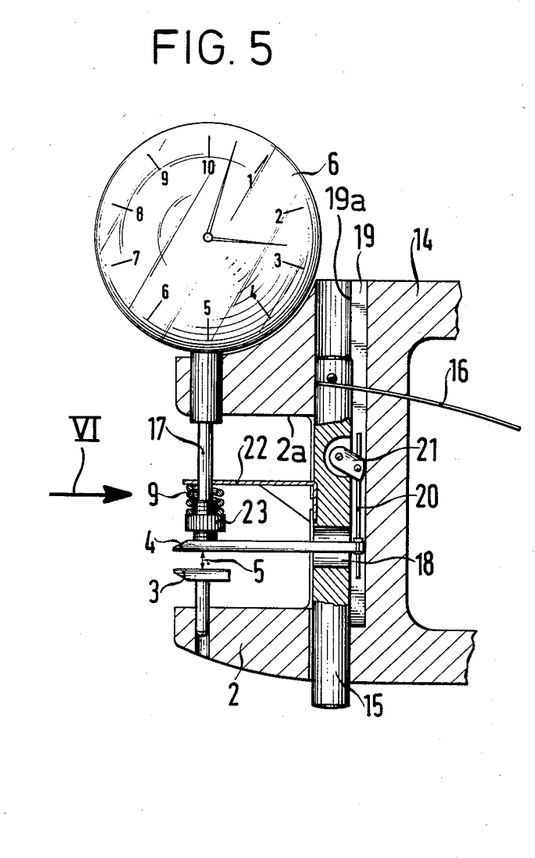
FIG. 5 is a partial section through a sliding caliper embodiment of the invention.
Figure 6:
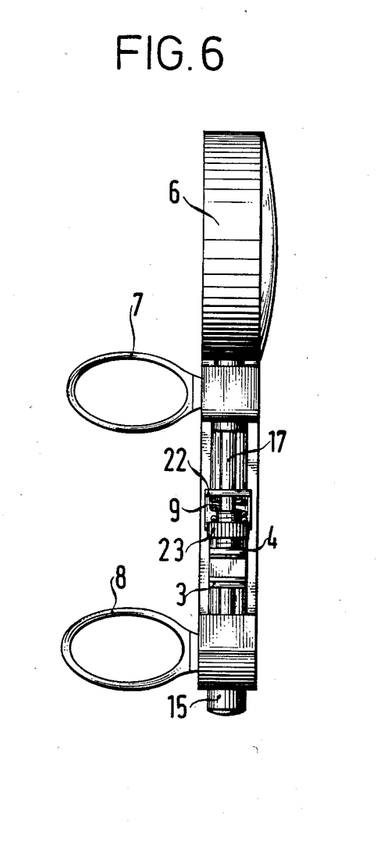
FIG. 6 is a view generally in the direction of the arrow VI—VI of FIG. 5.
Figure 7:
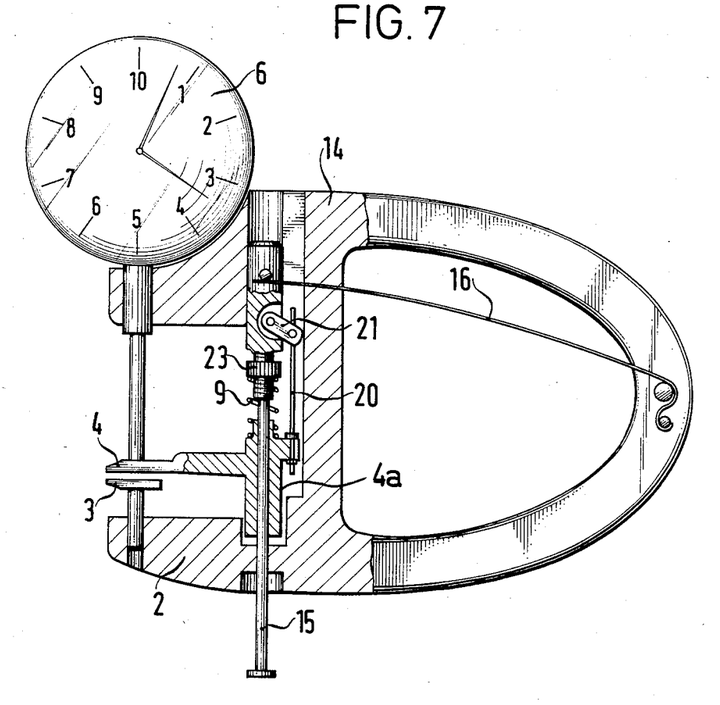
FIG. 7 is a view of another sliding caliper embodying the invention and shown in partial cross section.

The embodiment of FIGS. 5 and 6 operates in accordance with the slide-caliper principle. In this embodiment, a stirrup 14 which is only partially shown in FIG. 5 and is more completely shown in FIG. 7, is provided with a slide rod 15 which is shiftable relative to a fixed arm 2 and its contact plate 3. The slide rod 15 is displaceable by a finger ring 8 relative to another finger ring 7 fixed at an upper projection 2a upon which a conventional dial indicator 6 is mounted. The spindle 17 of the dial indicator 6 is threaded at its lower end and receives a nut or thimble 23 against which a spring 9 bears. This coil spring surrounds the spindle 17 and is seated against an angle bracket 22 fixed to the bar 15 and traversed by the spindle 17. A restoring spring 16 engages the rod 15 at one end and is anchored at its opposite end as shown in FIG. 7.

The other contact plate 4 is extended through a slot 18 in the rod 15. The orientation of the indicator 6 in line with the measurement region has been found to simplify the reading of the measurement and to improve the measuring comfort.

The contact plate 4 abuts the spindle 17 and is formed at its extension with a link rod 20 disposed in a groove 19 which opens, in turn, into the channel 19a in which the rod 15 is guided.

The link 20 is pivotally connected to a wedge or pawl 21 which is also rotatably or pivotally connected to the slide 15.

Upon relative movement of the contact plate 4 and the slide 15 in a sense tending to rotate the pawl 21 counterclockwise, the pawl lodges in the bottom of the groove 19 and prevents further downward displacement of the slide 15 and hence compression of the tissue received between the contact plates 3 and 4.

Using the finger rings 7 and 8, the contact plates 3 and 4 are brought against the tumor tissue whose thickness is to be measured and the tissue tends to urge the contact plate 4 upwardly relative to the slide 15 and thereby blocking further compression. In this case, therefore, the contact pressure at measurement is established by a locking of the contact plate and the locked measurement can be read directly from the dial indicator. The thimble 23 allows adjustment of the spring pressure of spring 9 by which the contact plate 4 is supported against the slide 15.

In FIG. 7, while a similar principle applies, the spring 9 is provided between a thimble 23 threaded onto the slide 15 and a sleeve 4a carrying the contact plate 4 and shiftable along the slide 15 while being connected via the link 20 to the swingable pawl 16. In this embodiment the finger ring 8 (not seen) can be connected to the portion of the slider 15 which projects below the stirrup 14. One of the advantages of this embodiment over the embodiments of FIGS. 5 and 6 is that the spring 9 and the thimble 23 are removed from the measurement region and hence the space between the contact plate is fully available for such measurement.

While in the embodiments of FIGS. 5-7 the yieldable contact plate is provided on the movable sensing arm, it should be understood that such yieldable contact plates can be provided on both sensing arms and that the yieldable plate can be provided on the fixed sensing arm.

Figure 8:
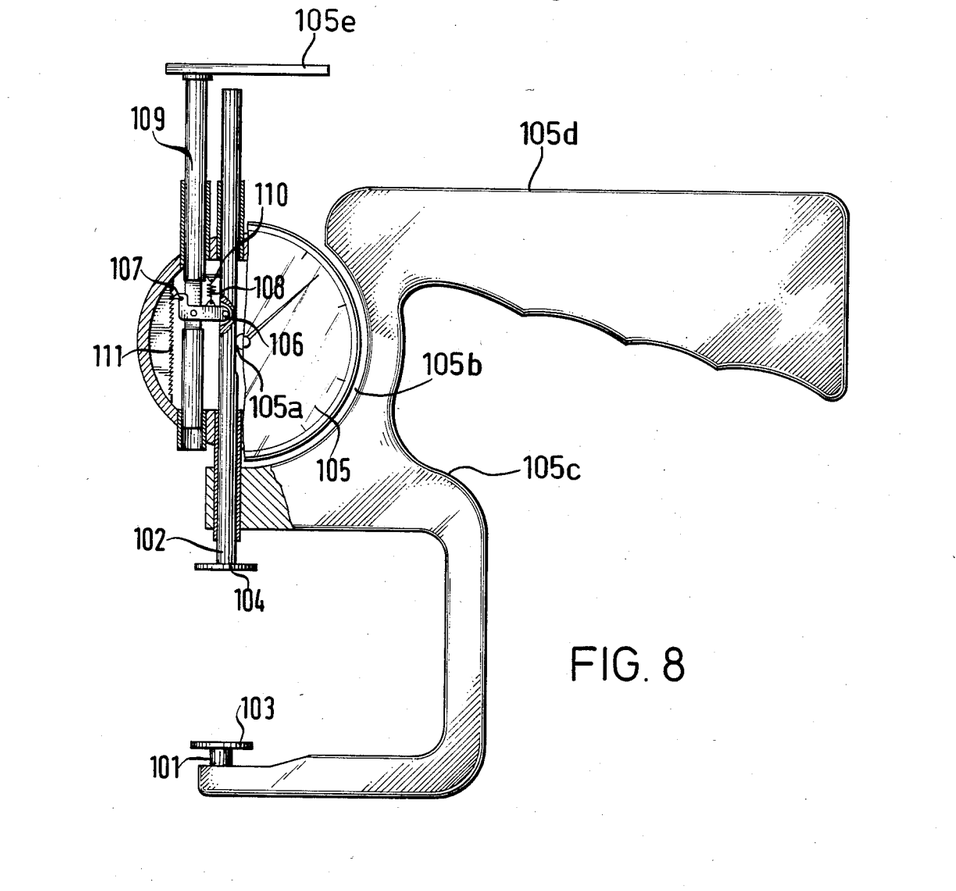
FIG. 8 is a partial section through another embodiment of the invention utilizing a dial indicator displaced by a rack.

FIG. 8 shows an embodiment of the invention utilizing a caliper arrangement having a fixed sensing arm 101 and a respective contact plate 103. In this case, the movable contact plate 104 is provided upon a spindle 102 which is connected by a rack and pinion arrangement shown only diagrammatically at 105a with the indicator needle of the dial indicator 105. The latter is mounted in a cut-out 105b of the caliper frame 105c which can have a handle 105d adapted to be gripped by the user. A thumb plate 105e is mounted upon an actuating rod 109 so that the latter can be pressed downwardly in the measurement operation.

The dial indicator is also equipped with a rack 111 which is engaged by a pawl or lever 107 fulcrumed on the rod 109 in a recess in the latter, this pawl being biased in the clockwise sense by a compression spring 108 resting against a seat 110 of the actuating arm 109. A pin 106 fixed at the spindle 102 engages a cut-out of the lever 107.

With increasing pressure against the object to be measured and thus with increasing resistance to further displacement of the contact plate 104, the spring 108 is further compressed and the lever 107 is caused to engage the rack 111. Upon engagement of the lever 107 with the rack 111, further displacement in the rod 102 of the rod 109 is blocked and, correspondingly, displacement of the rod 102 is blocked. This lock is released automatically when the device is removed from the object and the counterpressure of the object against the contact plate 104 is removed.

Figure 9:
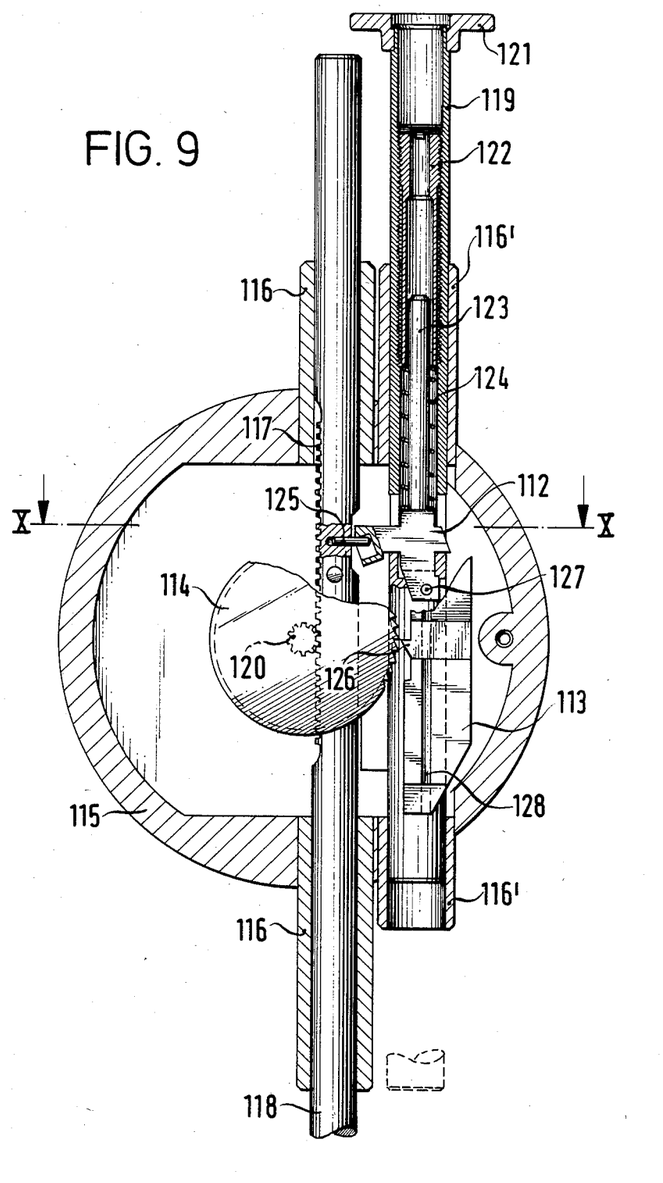
FIG. 9 is a sectional view through another embodiment of the instrument utilizing principles similar to those of FIG. 8 and in which at the desired measurement pressure the coupling of a pawl and ratchet or detent wheel is effected.
Figure 10:
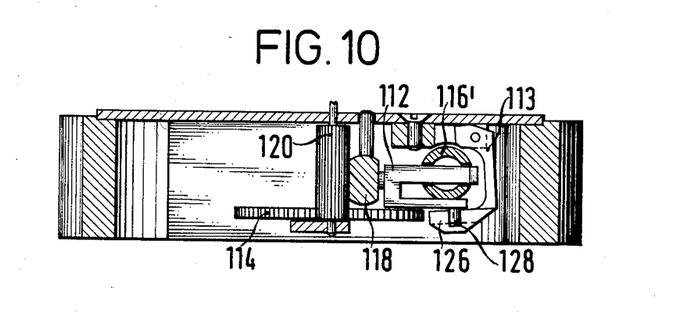
FIG. 10 is a cross section taken along the line X—X of FIG. 9.

In the embodiment of FIGS. 9 and 10, the locking mechanism is also effected by a pivotal lever 112 and a locking lever 113 which cooperates with a ratchet wheel 114.

The indicator housing 115 is formed with the guide sleeves 116 and 116', the former carrying a spindle 118 forming a rack 117 of a length sufficient for the entire range of the measurement. This rack engages a pinion 120 which can be coupled to the indicator arrow or hand to display the measurement on a scale not shown and centered on the axis of the pinion 120.

The actuatable rod 119, which has a thumb plate 121 enabling its displacement in the manner described, e.g. in connection with FIG. 8, has a measuring-force adjusting screw 122 which adjusts the position of a seat for the compression spring 124 which surrounds the spring-guiding rod 123 in this actuator. The spring 124 bears against a tiltable lever 112 to bias it in the clockwise sense. The tilting lever 112 transfers force via the coupling pin 125 to the slider 118.

When the resistance is such that the preset contact pressure is exceeded, lever 112 is swung in the clockwise sense so as to bring the ratchet lever 113 with its ratchet tooth 126 into engagement with the ratchet wheel 114. The engaging effects of the tooth and the wheel lie perpendicular to the direction of displacement of the members 118 and 119 so that a self-blocking of further movements occurs and is maintained as long as the pressing force is applied.

The horizontal left shank of the lever 112 tends to move upwardly and its vertical shank with the entrained pin 127 to the left. The entrainment pin 127 travels during the entire length in a measurement stroke in a groove 128 of the ratchet lever 113 and thus insures that the tilting of the lever 112 will effect the aforementioned movement of the lever 113 to the left.

This leftward movement of the lever 113 brings the tooth 126 into engagement with the ratchet wheel 114 which is mounted on the pinion 120 so that the entire assembly is form-locked against further movement. This locking is maintained as long as the applied force is greater than the preset measurement force and is released when the thumb pressure on plate 121 is released. Upon release of the pressing force, spring 124 retains the lever 112 in the counter-clockwise sense and swings the lever 113 into its starting position. A restoring spring (not shown) can return the members 118 and 119 to their original starting position as well.

We claim:

1. An instrument for measuring the size of an easily deformable object such as a body of tumor tissue, comprising:

a pair of relatively movable members defining a measuring caliper and formed at respective ends with contact plates adapted to receive said object between them;

an indicator operatively connected to at least a movable one of said plates and displaying a measurement of the size of said object as a function of the separation between said plates;

means for effecting relative displacement of said members to relatively displace said plates to embrace said object between them; and means interposed between one of said plates and the respective member for controlling the contact pressure of said one of said plates against said object, said means interposed between said one of said plates and said one of said members including a slider movable in a direction of measurement, and coupling means between said slider and said one of said plates for mechanically effecting a force-lock blocking further movement of said slider when a determined contact pressure is achieved.

2. An instrument for measuring the size of an easily deformable object such as a body of tumor tissue, comprising:
- a pair of relatively movable members defining a measuring caliper and formed at respective ends with contact plates adapted to receive said object between them;
- an indicator operatively connected to at least a movable one of said plates and displaying a measurement of the size of said object as a function of the separation between said plates;
- means for effecting relative displacement of said members to relatively displace said plates to embrace said object between them;
- means interposed between one of said plates and the respective member for controlling the contact pressure of said one of said plates against said object, said means interposed between said one of said plates and said one of said members including a slider movable in a direction of measurement, and coupling means between said slider and said one of said plates for mechanically effecting a force-lock blocking further movement of said slider when a determined contact pressure is achieved; and
- a restoring spring acting upon said slider for biasing same into a position corresponding to maximum separation of said plates.

3. The instrument defined in claim 2 wherein said means interposed between said one of said plates and the respective member further includes an adjustable-force spring for setting said contact pressure with which control is effective.

4. The instrument defined in claim 3 wherein said slider is provided with a seat for said adjustable force spring, further comprising a threaded thimble for adjusting the force with which said spring resists displacement of said one of said plates relative to said slider.

5. The instrument defined in claim 3 wherein said members are provided with finger rings enabling the displacement of said plates toward one another.

6. The instrument defined in claim 3 wherein said members are arms oriented such that such plates have substantially parallel surfaces in the measurement range.

7. An instrument for measuring the size of an easily deformable object such as a body of tumor tissue, comprising:
- a pair of relatively movable members defining a measuring caliper and formed at respective ends with contact plates adapted to receive said object between them;
- an indicator operatively connected to at least a movable one of said plates and displaying a measurement of the size of said object as a function of the separation between said plates;
- means for effecting relative displacement of said members to relatively displace said plates to embrace said object between them;
- means interposed between one of said plates and the respective member for controlling the contact pressure of said one of said plates against said object, said means interposed between said one of said plates and said one of said members including a slider movable in a direction of measurement, and coupling means between said slider and said one of said plates for mechanically effecting a force-lock blocking further movement of said slider when a determined contact pressure is achieved, said slider being provided with a lever pivotally mounted on said slider and engageable with a support receiving said slider, said one of said plates being connected with said lever by a rod swinging said lever into locking engagement with said support upon engagement of said one of said plates with said body of tumor tissue.

8. An instrument for measuring the size of an easily deformable object such as a body of tumor tissue, comprising:
- a support provided with a pair of parallel spaced-apart arms;
- a slide rod displaceable on said support in a direction transverse to said arms;
- respective means on said support and said rod engageable with fingers of a hand of a user for displacing said rod in one direction on said support;
- spring means on said support for biasing said rod relative to said support in the opposite direction;
- a fixed plate on one of said arms engageable with said object on one side thereof;
- an indicator on said support;
- a movable plate received between said arms and juxtaposed with said fixed plate, said movable plate being mounted so as to be entrained by said rod in said one direction but so as to be displaceable relative to said rod;
- means connecting said indicator with said movable plate; and
- a member mounted on said rod and actuatable by relative movement of said movable plate and said rod for forcibly locking said rod against said support upon engagement of said movable plate with an opposite side of said object.

9. The instrument defined in claim 8, further comprising spring means braced between said rod and said movable plate for displacement of said movable plate by said rod with a force determined by said spring means.

10. The instrument defined in claim 9, further comprising means for adjusting said force.

11. The instrument defined in claim 10 wherein said member is a lever pivotally mounted on said rod and said movable plate is coupled to said lever by a stem substantially parallel to said rod.

* * * * *